United States Patent
Smith et al.

(10) Patent No.: US 8,128,231 B2
(45) Date of Patent: Mar. 6, 2012

(54) ENHANCED LIFETIME ILLUMINATOR

(75) Inventors: Ronald T. Smith, Newport Coast, CA (US); Jaime R. Canedo, Irvine, CA (US); Mark Buczek, Oceanside, CA (US)

(73) Assignee: Novartis AG, Basel (CH)

(*) Notice: Subject to any disclaimer, the term of this patent is extended or adjusted under 35 U.S.C. 154(b) by 1176 days.

(21) Appl. No.: 11/867,932

(22) Filed: Oct. 5, 2007

(65) Prior Publication Data

US 2008/0086116 A1    Apr. 10, 2008

Related U.S. Application Data

(60) Provisional application No. 60/849,523, filed on Oct. 5, 2006.

(51) Int. Cl.
*A61B 3/00* (2006.01)
*A61B 3/10* (2006.01)

(52) U.S. Cl. .................. 351/221; 351/212

(58) Field of Classification Search .......... 351/200–246; 362/572
See application file for complete search history.

(56) References Cited

U.S. PATENT DOCUMENTS

| | | | | |
|---|---|---|---|---|
| 2007/0268720 A1* | 11/2007 | Rowe et al. | ............... | 362/572 |
| 2008/0183160 A1* | 7/2008 | Papac et al. | ............... | 606/4 |

* cited by examiner

*Primary Examiner* — Mohammed Hasan
(74) *Attorney, Agent, or Firm* — Keiko Ichiye

(57) ABSTRACT

An ophthalmic illuminator is disclosed, one embodiment comprising: an illumination source, wherein the illumination source produces an arc; a lens, such as a condensing lens, for focusing light produced by the illumination source arc; and an optical fiber for carrying the focused light to a surgical site, such as an eye. The illumination source is positioned offset from a longitudinal axis of the optical fiber to compensate for shifting of the illumination source arc over time. The offset position can be such that the illumination source is positioned in a vertically offset position from the longitudinal axis of the optical fiber. The longitudinal axis corresponds to the optical path axis of the optical fiber. The ophthalmic illuminator can further comprise a reflector for reflecting the light produced by the illumination source arc, wherein the reflector is positioned offset from the illumination source to decrease the rate of erosion of an illumination source cathode.

8 Claims, 5 Drawing Sheets

Fig. 6
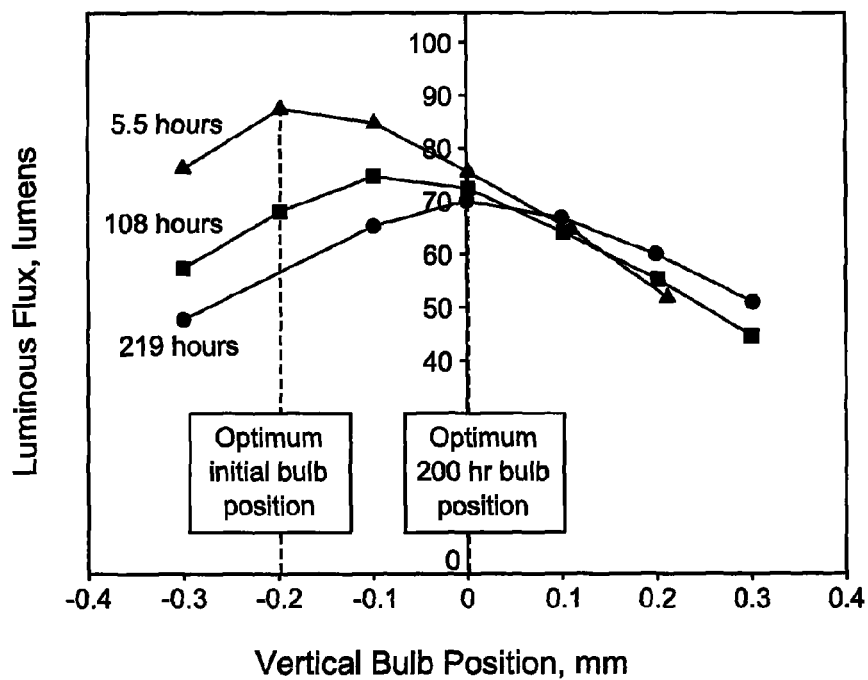
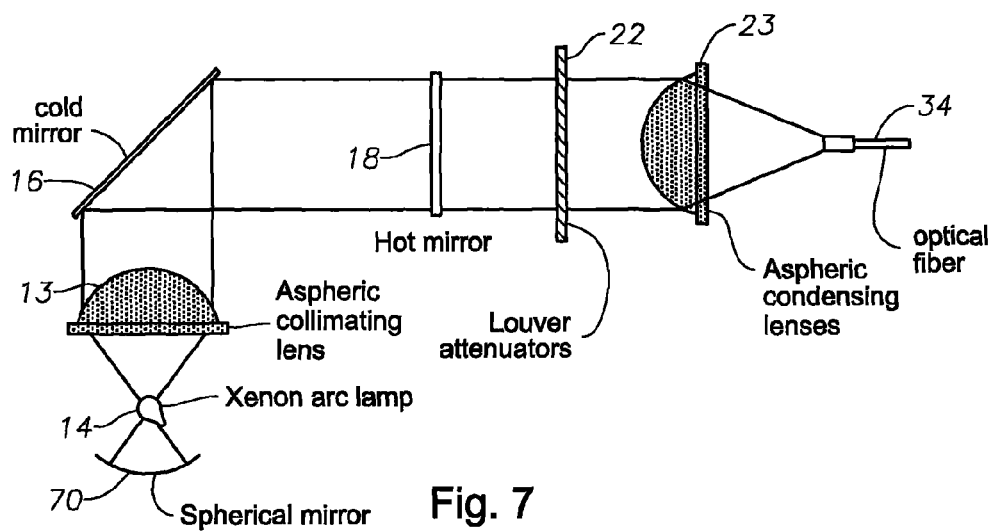
Fig. 7

ENHANCED LIFETIME ILLUMINATOR

CROSS-REFERENCE TO RELATED APPLICATIONS

This application claims priority under 35 U.S.C. §119 to U.S. Provisional Patent Application No. 60/849,523 filed Oct. 5, 2006, the entire contents of which are incorporated herein by reference.

TECHNICAL FIELD OF THE INVENTION

The present invention relates generally to the field of illumination systems. In particular, the present invention relates to ophthalmic illumination systems and, more particularly, to a method and system for enhancing the useful lifetime of an ophthalmic illumination system.

BACKGROUND OF THE INVENTION

Many ophthalmic surgical procedures require illuminating a portion of a patient's eye so that a surgeon can observe a surgical site. Various different types of instruments are known and available for use by an ophthalmic surgeon to illuminate the interior of the eye. For example, the handheld (probe) portion of a typical ophthalmic illuminator comprises a handle having a projecting tip and a length of optical fiber that enters a proximal end of the handle and passes through the handle and the tip to a distal end of the tip, from which light traveling along the optical fiber can project. The proximal end of the optical fiber can be optically coupled to a light source, such as in a high brightness illuminator, to receive the light that is transmitted through the fiber. These types of handheld illuminators are typically used by inserting the probe tip through a small incision in the eye. In this way, light from the illuminator light source is carried along the optical fiber, through the handpiece and emitted from the distal end of the probe (fiber) to illuminate the surgical site for the surgeon. Ophthalmic illumination systems that use a length of optical fiber to carry and direct light from a light source to a surgical site are well known in the art.

Such ophthalmic illumination systems typically comprise a handheld portion including a probe, to deliver illumination from a light source housed in an enclosure. The enclosure typically houses the light source and associated optics that guide light from the light source to the optical fiber of a probe, a power supply, electronics with signal processing, and associated connectors, displays and other interfaces, as known to those having skill in the art. While some ophthalmic illumination systems use other types of lamps as a light source, a preferred light source is a xenon lamp.

An ophthalmic illumination system xenon lamp typically has a relatively small arc (e.g., about 0.18 mm width for an Osram 75 W xenon bulb at zero hours operating time). Optics within the illumination system are used to focus an image of the arc onto the optical fiber of the probe and the xenon bulb must be precisely aligned to ensure that an optimum amount of light is coupled into the optical fiber, and hence an optimum luminous flux emerges from the fiber. The optical fiber core diameter is selected to be large enough that the arc image will fit within the fiber core area. However, as the xenon bulb ages, the bulb cathode degrades and moves away from the bulb anode. As the cathode degrades, the arc grows in size, decreases in peak luminance and the arc center moves away from the anode.

The xenon bulb is positioned so that the arc image will fall on the optical fiber core entrance surface. In prior art illumination systems, the xenon bulb is positioned such that maximum fiber throughput is achieved at zero hours of operation (i.e., beginning of life of the xenon bulb). However, the arc can move (due to cathode degradation) in excess of about 250 microns during the first 200 hours of operation in a typical illumination system. Therefore, if the xenon bulb is aligned for maximum fiber throughput at zero hours, the arc movement (which can result in much of the arc image moving outside of the fiber core area) combined with the decrease in arc peak luminance will result in an appreciable drop in fiber throughput, and hence in an appreciable drop in illumination at the surgical site.

One way of solving this problem in prior art ophthalmic illumination systems is to increase the diameter of the proximal end of the optical fiber core. However, increasing the diameter of the optical fiber has several disadvantages. One disadvantage is that the increased fiber diameter results in a stiffer optical fiber, which is not as easy to manipulate in an operating environment. Further, a larger diameter fiber is more expensive because more fiber material is used per unit length of optical fiber. Even further, a larger diameter fiber may be greater than that allowed by the probe requirements. For example, a 20 gauge ophthalmic illuminator probe (0.355 inch cannula outer diameter) can accommodate a maximum diameter of the fiber core and cladding of 0.0295 inches. Further still, undesired dissipation of the light from the light source can result from allowing a tightly focused arc image to expand into a larger diameter beam as defined by the larger diameter fiber. Once this light concentration is lost, it cannot be recaptured. If the optical fiber tapers to a smaller diameter downstream from its proximal end, the ability of the light to efficiently transmit through the tapered fiber will depend on the concentration of the light prior to the start of the fiber taper. If the arc image is allowed to spread spatially and dissipate its light concentration, the light will transmit less efficiently into the tapered fiber portion.

Therefore, a need exists for a method and system for enhancing the useful lifetime of an ophthalmic illumination system that can reduce or eliminate the problems of prior art ophthalmic illumination systems discussed above.

BRIEF SUMMARY OF THE INVENTION

The embodiments of the method and system for enhancing the useful lifetime of an ophthalmic illumination system of this invention substantially meet these needs and others. One embodiment of the present invention comprises an ophthalmic illuminator comprising: an illumination source, wherein the illumination source produces an arc; a lens, such as a condensing lens, for focusing light produced by the illumination source arc; and an optical fiber for carrying the focused light to a surgical site, such as an eye. The illumination source is positioned offset from a longitudinal axis of the optical fiber to compensate for shifting of the illumination source arc over time. The offset position can be such that the illumination source is positioned in a vertically offset position from the longitudinal axis of the optical fiber. The longitudinal axis corresponds to the optical path axis of the optical fiber. The ophthalmic illuminator can further comprise a reflector for reflecting the light produced by the illumination source arc, wherein the reflector is positioned offset from the illumination source to decrease the rate of erosion of an illumination source cathode.

The ophthalmic illuminator can be a high brightness illuminator and the illumination source can be a xenon lamp. The ophthalmic illuminator can also comprise a connector for aligning the light exiting the focusing lens with the optical fiber; a hand piece carrying the optical fiber, the hand piece capable of being manipulated in a hand; and a probe for carrying the optical fiber into the surgical site. The connector can be attached (and detached) to a port for aligning the light exiting the focusing lens with the optical fiber Other embodiments of this present invention can include a method for enhancing the useful lifetime of an ophthalmic illuminator by offsetting a xenon lamp arc in accordance with the teachings of this invention.

Embodiments of this invention can be implemented within a surgical machine or system for use in ophthalmic or other surgery. In particular, it is contemplated that the method and system for enhancing the useful lifetime of an ophthalmic illumination system of this invention can be implemented in, or incorporated into, any ophthalmic illumination system in which it is desirable to efficiently couple a xenon light source optical beam to a small diameter optical fiber. Other uses for the method and system of this invention will be apparent to those having skill in the art.

BRIEF DESCRIPTION OF THE SEVERAL VIEWS OF THE DRAWINGS

A more complete understanding of the present invention and the advantages thereof may be acquired by referring to the following description, taken in conjunction with the accompanying drawings, in which like reference numbers indicate like features and wherein:

FIG. 6 is a graph showing luminous flux versus vertical illumination source bulb position for various operating times;

FIG. 7 is a more detailed diagrammatic representation of a portion of illuminator system 10 of FIG. 1 further comprising a retro-reflecting mirror 70 behind the illumination source 14 arc.

DETAILED DESCRIPTION OF THE INVENTION

Preferred embodiments of the present invention are illustrated in the FIGUREs, like numerals being used to refer to like and corresponding parts of the various drawings.

The various embodiments of the method and system for enhancing the useful lifetime of an ophthalmic illumination system of this invention provide for an enhanced fiber optic illuminator that has an optimized throughput after a preset number of operating hours (e.g., 200 hrs) that meets the throughput requirements desired for the illumination system. In some embodiments, the throughput during the initial operating period (e.g., up to 200 hrs) can be at least as high as the throughput at a desired end of the initial operating period (e.g., at 200 hrs). Embodiments of the present invention can further provide a fiber throughput that is relatively constant during the initial operating period. By initially misaligning the xenon lamp arc in a direction towards the lamp anode, an optimum throughput during the initial operating period can be achieved, as well as equal or better throughput during the illuminator lifetime after the initial operating period.

Embodiments of the present invention can include a fiber optic illumination system comprising a xenon light source in which the xenon arc lamp bulb has been offset (e.g., positioned in a vertically offset position) from an axis corresponding to the optical path axis of an optical fiber (e.g., from the initial position of prior art systems as known to those having skill in the art) to move the arc off-axis at the beginning of life of the xenon light source. The xenon light source can be any xenon lamp having the characteristics required to provide high intensity light for an illuminator, such as an ophthalmic illuminator, as will be known to those having skill in the art. For example, the xenon light source can be an Osram 75 W xenon bulb.

By initially positioning the xenon lamp arc off-axis at the zero operating hour time (the initial position), as the xenon lamp arc location moves away from the anode due to cathode degradation as the lamp ages, the arc will move increasingly on-axis and the coupling efficiency into the optical fiber will increase. This effect will tend to cancel out the effect of decreasing arc peak luminance as operation time increases so that the overall light throughput through the optical fiber (e.g., a handheld illuminator probe fiber) will tend to remain about constant as the lamp ages. The initial position of the xenon lamp is determined by first positioning the xenon lamp bulb to achieve a maximum light flux through an output optical fiber. The bulb (or bulb\mirror assembly) is then vertically misaligned by a prescribed amount and set in place. The desired initial position of the bulb is determined as described below.

Figure 1:
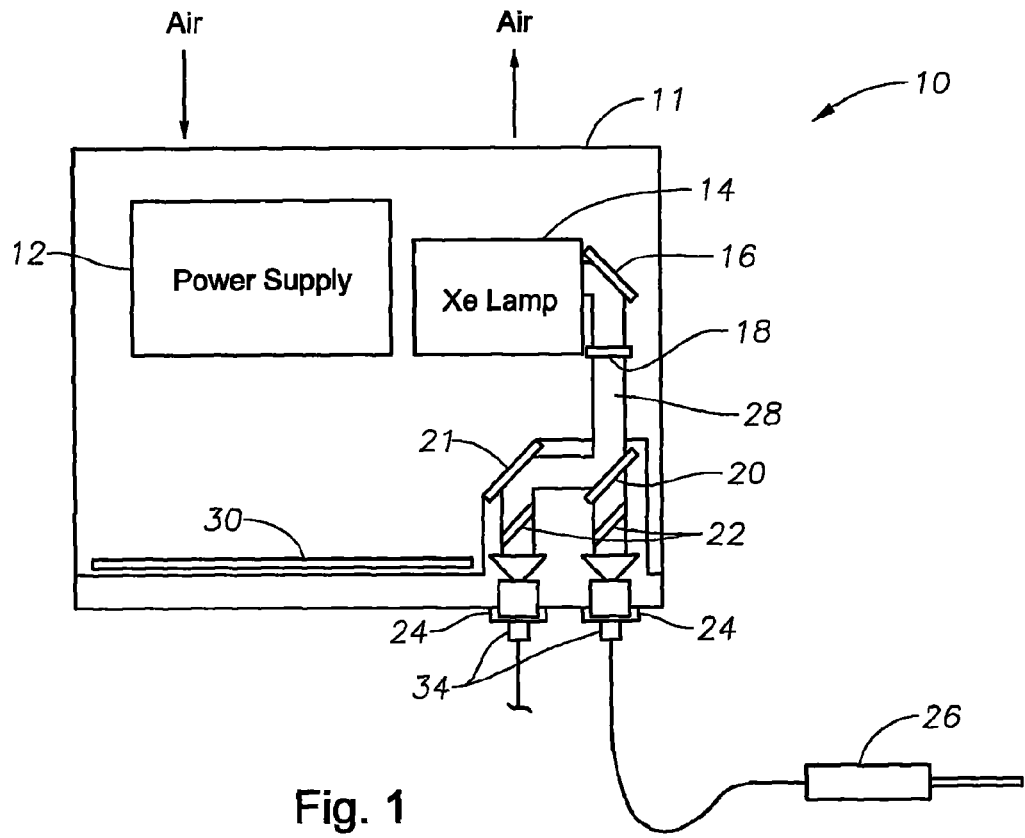
FIG. 1 is a diagrammatic representation of one embodiment of an enhanced high brightness ophthalmic illuminator system of the present invention.

FIG. 1 is a diagrammatic representation of one embodiment of an enhanced high brightness ophthalmic illuminator system of the present invention. Illuminator system 10 comprises power supply 12 and illumination source 14, cold mirror 16, a hot mirror 18, a beam splitter 20, mirror 21, optical fiber ports 24 and attenuators 22. Illuminator system 10 also can comprise one or more optical fiber probes 26 for receiving and transmitting light from illumination source 14 to a surgical site. Optical fiber probes 26 comprise the handheld portion of the illuminator system 10, including optical fiber 34, which is optically coupled to the illumination source 14 within enclosure 11. High brightness illuminator system 10 is exemplary only and is not intended to limit the scope of the present invention in any way. The embodiments of the present invention can be used to enhance any such ophthalmic illuminator, medical laser, or any other system or machine in which it is desirable to extend the useful lifetime of an illumination source.

Optical source 14 of illuminator system 10 in this example comprises a xenon lamp, but it can comprise any suitable light source as known to those having skill in the art in which the cathode degrades with age affecting the arc position and intensity. Xenon lamp 14 emits light beam 28, which is directed along the optical path comprising cold mirror 16, hot mirror 18, beam splitter 20, mirror 21, attenuators 22, and optical fiber ports 24. In this example, beam splitter 20 splits light beam 28 into two optical paths to provide for two optical probes 26 if desired. Cold mirror 16 and hot mirror 18 combine to remove the infrared and UV components of light beam 28 (heat) and provide a cool visible light beam 28 to the downstream optical components, as will be familiar to those skilled in the art. Attenuators 22 attenuate optical beam 28. Attenuators 22 can each be custom designed for its respective optical path and need not be identical, though they can be. Further, each attenuator 22 can be independently controlled via, for example, PCB 30.

Although high brightness illuminator system 10 is shown comprising two optical fiber ports 24 (with aspheric lenses or other focusing elements), it will be known to those having skill in the art that a single optical port 24 or multiple optical ports 24 can be implemented within illuminator system 10. Illuminator system 10 further comprises a printed circuit board ("PCB") 30, or its electronic equivalent, to provide signal processing and control functions. PCB 30 can be implemented in any manner and configuration capable of performing the desired processing and control functions described herein, as will be apparent to those having skill in the art. Optical ports 24 comprise a receptacle to receive the proximal end of an optical fiber 34 corresponding to a fiber probe 26, which is inserted into the high brightness illuminator enclosure 11 and optically coupled to illumination source 14 to direct light onto a desired site.

Figure 2:
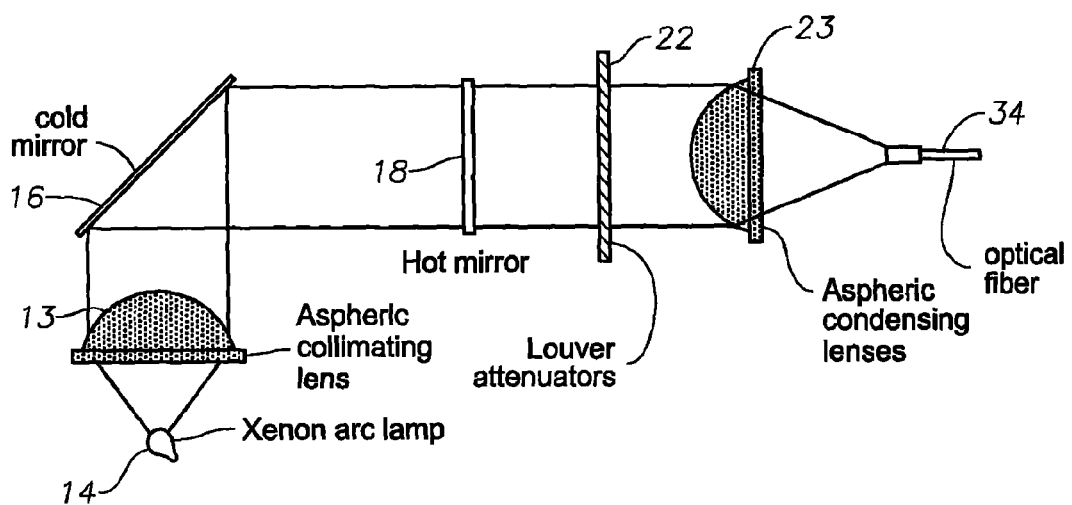
FIG. 2 is a more detailed diagrammatic representation of a portion of illuminator system 10 of FIG. 1.

FIG. 2 is a more detailed diagrammatic representation of a portion of illuminator system 10 of FIG. 1. Light emitted from the illumination source 14 arc region (e.g., a xenon arc lamp) is collimated by the collimating lens 13, and filtered by the cold mirror 16, hot mirror 18 and attenuator 22. The light is then focused by the condensing lens 23 (which can be part of an optical fiber port 24) into optical fiber 34. Coupling the light from illumination source 14 into optical fiber 34 is efficient if the arc region is very small, the magnification provided by the illuminator system optics is small enough that the area of the arc image on the optical fiber 34 fits the core area of the optical fiber 34 and the illumination source 14 bulb is aligned so that the arc image size is kept small and the arc image fits within the core area of the optical fiber.

Figure 3:
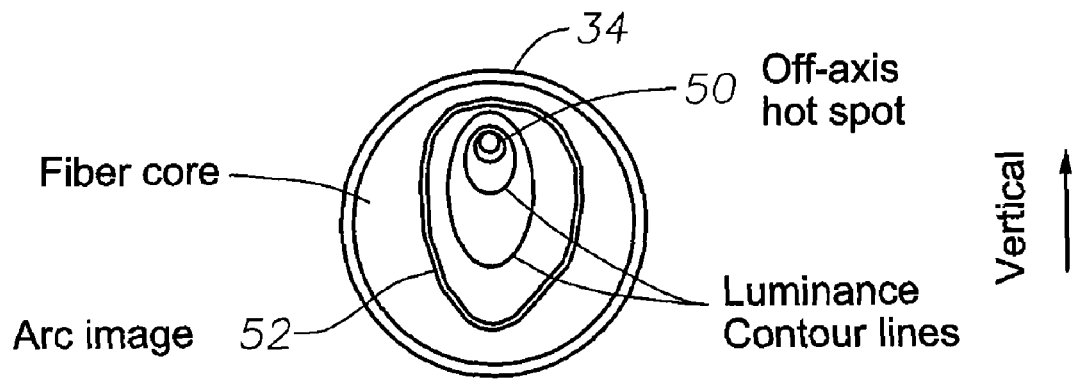
FIG. 3 illustrates one example of a the arc image position for an illumination source 14 comprising an Osram 75 W xenon bulb.

FIG. 3 illustrates one example of the optical coupling to a fiber of the light from an illumination source 14 comprising an Osram 75 W xenon bulb. As shown in FIG. 3, the light source 14 arc is tear-drop shaped in this example with the long axis vertical and having an approximate width of about 0.18 mm. The optical fiber 34, in this example, has a 1.14 mm diameter proximal end and the optical components of illuminator system 10 provide a magnification of about 1.41. In this example, the arc image 52 fits within the optical fiber 34 core area, and due to the tear-drop shape of the arc, an optimum fiber throughput occurs when the hot-spot 50 is vertically decentered relative to the optical fiber 34 longitudinal axis.

Figure 4:
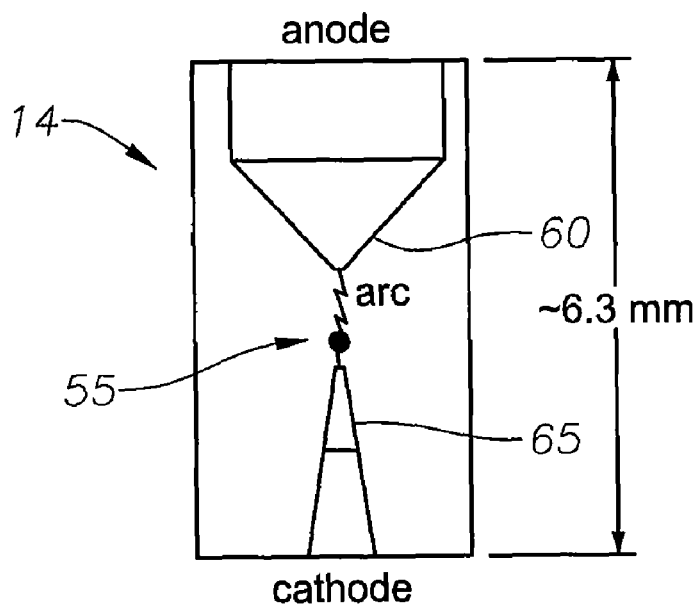
FIG. 4 is a close-up view of the arc region of an illumination source 14 comprising a xenon lamp.

FIG. 4 is a close-up view of the arc region of an illumination source 14 comprising a xenon lamp. Arc 55 is created between anode 60 and cathode 65. As can be seen from FIG. 4, arc 55 is closer to the cathode 65. Arc 55 emits the light provided by illuminator system 10.

Figure 5:
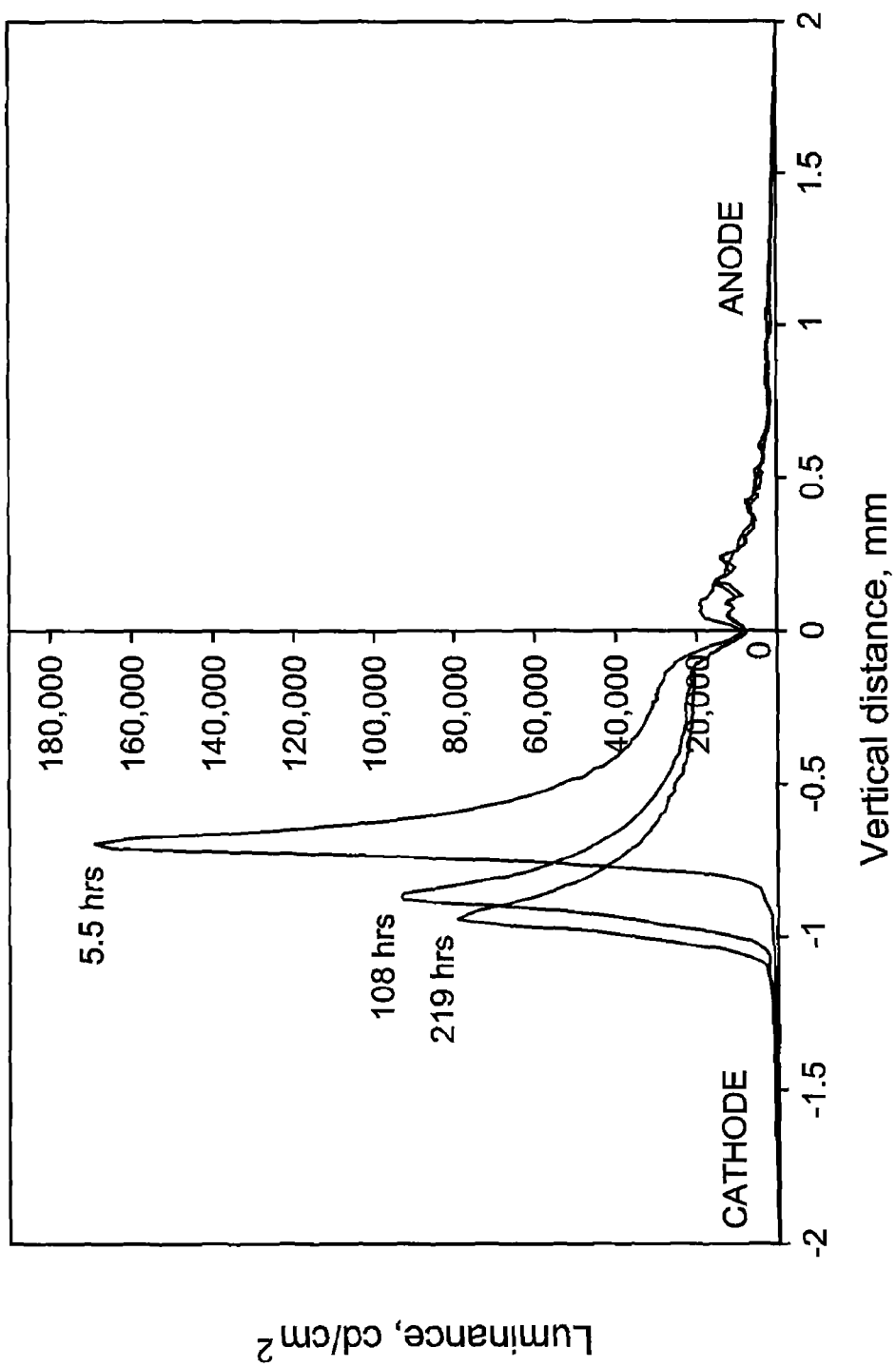
FIG. 5 is a graph showing the resultant change in measured arc luminance versus operating time for the example of an Osram 75 W xenon bulb illumination source.

As the illumination source 14 bulb ages, the tip of the cathode 65 erodes away, causing the tip of cathode 65 to move in a downward direction (for a typical installation) away from the anode 60 and to become blunter. As the cathode 65 erodes, the arc 55 grows in size, decreases in peak luminance, and also moves in the same direction as the cathode 65 away from anode 60, causing a monotonic and rapid decrease in the illuminator system light throughput. The resultant change in measured arc luminance versus operating time for the example of an Osram 75 W bulb is show in the graph of FIG. 5. It is worth noting that although the examples provided herein involve an Osram 75 W xenon bulb, the analysis and results are expected to be comparable for other such illumination sources.

The arc 55 position can shift by about 250 microns during the first 200 hours of bulb operation due to such cathode degradation. Therefore, if the illumination source 14 is aligned for maximum fiber throughput at zero hours of system operation, the arc 55 movement combined with the decrease in arc 55 peak luminance can cause significant degradation in fiber throughput. The embodiments of the present invention comprise an illumination source 14 bulb offset (e.g., vertically misaligned) relative to the longitudinal axis of an optical fiber 34, so that the illumination source 14 performance at the end of a desired initial high-performance period of operation (e.g., about 200 hours) is at a desired optimal level. At zero hours, the arc 55 can be positioned to have a desired optimum peak luminance, but will be vertically misaligned. At the end of the initial period of operation, the arc 55 will have a degraded peak luminance (see FIG. 5), but will achieve a position of approximate vertical alignment. These two effects can tend to cancel each other out so that the fiber throughput at zero hours, at the end of the initial period of operation (e.g., 200 hours) and at times in between will be about the same (approximately constant).

The effects described herein have been demonstrated theoretically by analyzing an illuminator system 10 having an Osram 75 W xenon illumination source 14 using Zemax optical ray tracing software. The results of one such analysis are illustrated in FIG. 6.

As shown in FIG. 6, if the vertical portion of the illumination source 14 bulb is positioned to achieve a desired optimum throughput at 5.5 hours of operation, the bulb throughput will decrease by about 35% after about 219 hours. However, if the vertical position of the bulb is adjusted to achieve a desired optimum throughput at 219 hours, the 5.5 hour to 219 hour throughput decrease is less than about 7%. The throughput in such a case degrades much more slowly and monotonically between about 5.5 and about 219 hours.

In some embodiments, an illuminator system 10 can comprise a retro-reflecting mirror (or other reflector) 70 behind the illumination source 14 arc, as shown in FIG. 7. The retro-reflecting mirror 70 can be positioned such that it is slightly misaligned (offset) vertically relative to the illumination source 14 bulb in order to keep the majority of reflected arc 55 image power off the cathode 65, and thus decrease the rate of cathode 65 erosion.

Figure 8A:
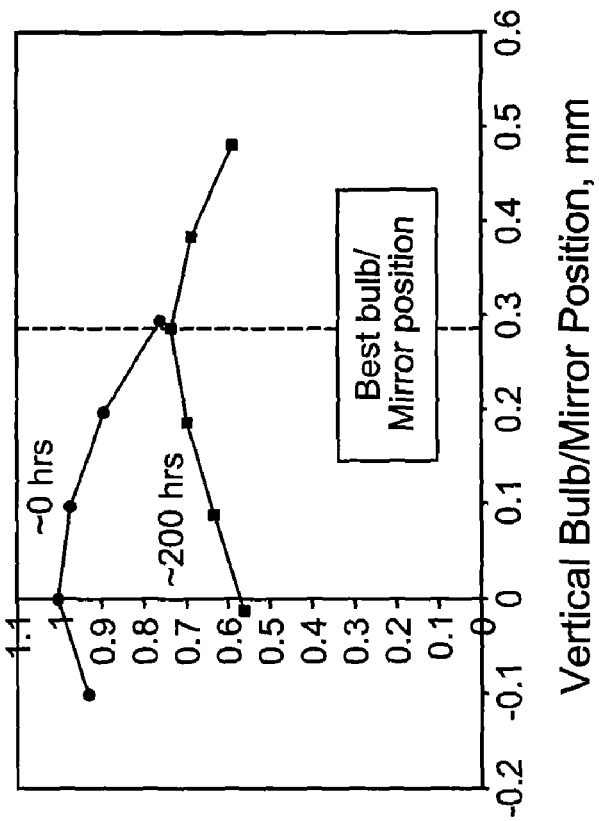
FIGS. 8A and 8B are graphs illustrating the results of a comparison between a theoretical Zemax software simulation and experimental data.
Figure 8B:
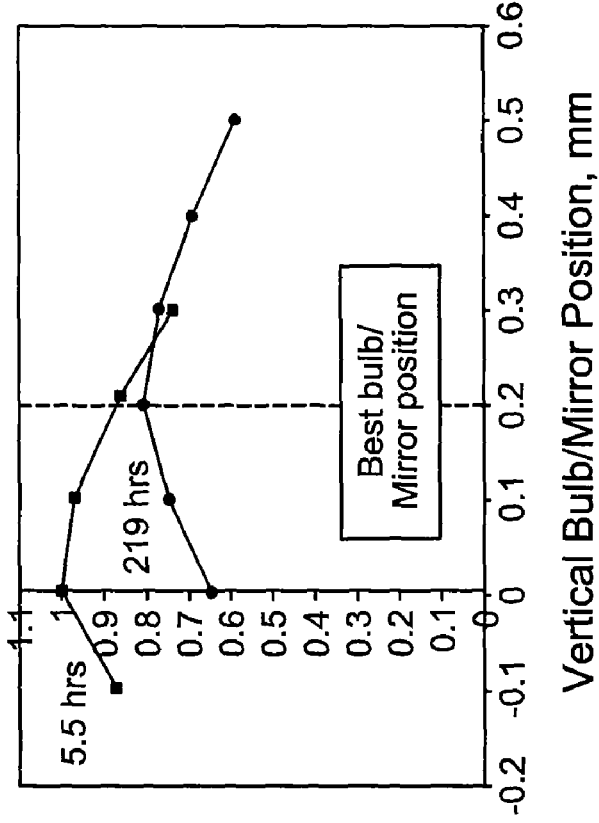

FIGS. 8A and 8B illustrate the results of a comparison between a theoretical Zemax software simulation and experimental data (on a different Osram 75 W xenon bulb than the theoretical simulation). The results for about zero hours and about 200 hours operation time (with the peak throughput value at about zero hours operation time normalized to 1) show excellent agreement between theory and experiment.

Various embodiments of the present invention thus provide for improved optical coupling to and light transmission through a small gauge optical fiber. Further, the embodiments of this invention provide the ability to significantly reduce the decay in coupling efficiency with time as a xenon light source ages. The embodiments of the present invention can be incorporated into any xenon lamp based optical device, such as an ophthalmic illuminator, where optical coupling of a light beam into a small gauge optical fiber is desired.

The present invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims.

What is claimed is:

1. An ophthalmic illuminator comprising:
   an illumination source, wherein the illumination source produces an arc;
   a lens for focusing light produced by the illumination source arc; and
   an optical fiber for carrying the focused light to a surgical site;
   wherein the illumination source is offset from a longitudinal axis of the optical fiber to yield a hot spot that is not at the longitudinal axis in order to compensate for shifting of the illumination source arc over time; further comprising:
   a reflector for reflecting the light produced by the illumination source arc, wherein the reflector is positioned offset from the illumination source to decrease the rate of erosion of an illumination source cathode.

2. The ophthalmic illuminator of claim 1, wherein the illuminator is a high brightness illuminator.

3. The ophthalmic illuminator of claim 1, wherein the illumination source is a xenon lamp.

4. The ophthalmic illuminator of claim 1 further comprising:
   a connector for aligning the light exiting the focusing lens with the optical fiber;
   a hand piece carrying the optical fiber, the hand piece capable of being manipulated in a hand; and
   a probe for carrying the optical fiber into the surgical site.

5. The ophthalmic illuminator of claim 4, further comprising:
   a port attachable to and detachable from the connector, the port for aligning the light exiting the focusing lens with the optical fiber.

6. The ophthalmic illuminator of claim 1, wherein the offset position of the illumination source is a position such that the illumination source is positioned in a vertically offset position from the longitudinal axis of the optical fiber, and wherein the longitudinal axis corresponds to the optical path axis of the optical fiber.

7. The ophthalmic illuminator of claim 1, wherein the lens is a condensing lens.

8. The ophthalmic illuminator of claim 1, wherein the surgical site is an eye.

* * * * *